United States Patent
Wilford et al.

(10) Patent No.: US 8,979,915 B2
(45) Date of Patent: Mar. 17, 2015

(54) SEPARABLE SYSTEM FOR APPLYING COMPRESSION AND THERMAL TREATMENT

(75) Inventors: Michael L. Wilford, Chicago, IL (US); Aaron Stein, Middletown, CT (US); John Lewis, Monson, MA (US); Fernando Ubidia, Ludlow, MA (US)

(73) Assignee: Pulsar Scientific, LLC

( * ) Notice: Subject to any disclaimer, the term of this patent is extended or adjusted under 35 U.S.C. 154(b) by 803 days.

(21) Appl. No.: 13/089,161

(22) Filed: Apr. 18, 2011

(65) Prior Publication Data

US 2011/0257565 A1 Oct. 20, 2011

Related U.S. Application Data

(60) Provisional application No. 61/342,759, filed on Apr. 19, 2010.

(51) Int. Cl.
*A61F 7/02* (2006.01)
*A61H 9/00* (2006.01)

(52) U.S. Cl.
CPC ...... *A61H 9/0078* (2013.01); *A61H 2201/0157* (2013.01); *A61H 2201/0207* (2013.01); *A61H 2201/0242* (2013.01); *A61H 2201/5002* (2013.01); *A61H 2201/5015* (2013.01); *A61H 2201/5046* (2013.01); *A61H 2201/5097* (2013.01); *A61H 2209/00* (2013.01)
USPC ........ 607/104; 417/199.1; 417/313; 417/360; 417/426; 601/15; 601/148; 607/114

(58) Field of Classification Search
CPC .......... F04B 23/02; F04B 23/04; F04B 23/06; F04C 14/00
USPC ........... 417/63, 199.1, 360, 361, 363, 423.15, 417/423.14, 426, 201, 313; 601/9, 11, 15, 601/16, 148–152, 154, 160; 607/104, 114
See application file for complete search history.

(56) References Cited

U.S. PATENT DOCUMENTS

| | | | | |
|---|---|---|---|---|
| 4,149,529 A | * | 4/1979 | Copeland et al. | 601/17 |
| 4,480,890 A | * | 11/1984 | McGlew | 439/488 |
| 4,938,208 A | | 7/1990 | Dye | |
| 5,230,335 A | | 7/1993 | Johnson, Jr. et al. | |
| 5,314,455 A | | 5/1994 | Johnson, Jr. et al. | |
| 5,350,317 A | * | 9/1994 | Weaver et al. | 439/500 |
| 5,354,260 A | | 10/1994 | Cook | |
| 5,411,541 A | | 5/1995 | Bell et al. | |
| 5,437,610 A | | 8/1995 | Cariapa et al. | |
| 5,466,250 A | | 11/1995 | Johnson, Jr. et al. | |
| 5,584,798 A | | 12/1996 | Fox | |
| 5,588,955 A | | 12/1996 | Johnson, Jr. et al. | |
| 5,711,155 A | | 1/1998 | DeVilbiss et al. | |
| 5,711,760 A | | 1/1998 | Ibrahim et al. | |
| 5,865,841 A | * | 2/1999 | Kolen et al. | 607/104 |

(Continued)

*Primary Examiner* — Bryan Lettman
*Assistant Examiner* — Charles W Nichols
(74) *Attorney, Agent, or Firm* — Olson & Cepuritis Ltd.

(57) ABSTRACT

The invention relates to a separable device for the application of compression and thermal therapy to a patient. A first section includes a reservoir, liquid pump and a thermal exchange system for the application of thermal therapy as well as a dock. The second section of the device includes an air compressor and at least one controller for the application of compression therapy and can be operated independently from the first section. Additionally, the second section may be engaged with a dock of the first section.

18 Claims, 9 Drawing Sheets

(56) References Cited

U.S. PATENT DOCUMENTS

| | | |
|---|---|---|
| 5,890,371 A | 4/1999 | Rajasubramanian et al. |
| 5,891,065 A | 4/1999 | Cariapa et al. |
| 5,894,615 A | 4/1999 | Alexander |
| 5,968,072 A | 10/1999 | Hite et al. |
| 5,989,204 A | 11/1999 | Lina |
| 5,989,285 A | 11/1999 | DeVilbiss et al. |
| 6,058,712 A | 5/2000 | Rajasubramanian et al. |
| 6,080,120 A | 6/2000 | Sandman et al. |
| 6,141,043 A | 10/2000 | Suzuki et al. |
| 6,290,662 B1 | 9/2001 | Morris et al. |
| 6,322,530 B1 | 11/2001 | Johnson, Jr. et al. |
| 6,352,550 B1 | 3/2002 | Gildersleeve et al. |
| 6,358,219 B1 | 3/2002 | Arkans |
| 6,440,093 B1 | 8/2002 | McEwen et al. |
| 6,462,949 B1 | 10/2002 | Parish, IV et al. |
| 6,551,280 B1 | 4/2003 | Knighton et al. |
| 6,551,347 B1 | 4/2003 | Elkins |
| 6,592,534 B1 | 7/2003 | Rutt et al. |
| 6,685,661 B2 | 2/2004 | Peled |
| 6,736,787 B1 | 5/2004 | McEwen et al. |
| 6,755,798 B2 | 6/2004 | McCarthy et al. |
| 6,786,879 B1 | 9/2004 | Bolam et al. |
| 6,817,363 B2 | 11/2004 | Biondo et al. |
| 6,865,825 B2 | 3/2005 | Bailey, Sr. et al. |
| 6,893,409 B1 | 5/2005 | Lina |
| 6,946,988 B2 * | 9/2005 | Edwards et al. ............... 341/176 |
| 6,957,697 B2 | 10/2005 | Chambers |
| 7,173,513 B2 | 2/2007 | Laaser |
| 7,207,959 B1 | 4/2007 | Chandran |
| 7,211,104 B2 | 5/2007 | Edelman |
| 7,276,037 B2 | 10/2007 | Ravikumar |
| 7,282,038 B2 | 10/2007 | Gillis et al. |
| 7,343,916 B2 | 3/2008 | Biondo et al. |
| 7,354,410 B2 | 4/2008 | Perry et al. |
| 7,354,411 B2 | 4/2008 | Perry et al. |
| 7,396,345 B2 | 7/2008 | Knighton et al. |
| 7,442,175 B2 | 10/2008 | Meyer et al. |
| 7,488,919 B2 | 2/2009 | Gagas et al. |
| 7,542,744 B2 | 6/2009 | Zuehlsdorff |
| 7,559,908 B2 | 7/2009 | Ravikumar |
| D603,036 S | 10/2009 | Boswell |
| 7,637,879 B2 | 12/2009 | Barak et al. |
| 7,641,623 B2 | 1/2010 | Biondo et al. |
| 7,648,472 B2 | 1/2010 | McCarthy et al. |
| 7,691,084 B2 | 4/2010 | Knighton et al. |
| 7,850,629 B2 | 12/2010 | Ravikumar |
| 7,909,861 B2 | 3/2011 | Balachandran et al. |
| 8,052,626 B2 * | 11/2011 | Huster et al. ................... 601/41 |
| 2002/0134544 A1 | 9/2002 | DeVilbiss et al. |
| 2002/0134570 A1 * | 9/2002 | Franklin-Lees et al. ........ 174/58 |
| 2003/0139255 A1 | 7/2003 | Lina |
| 2003/0191437 A1 | 10/2003 | Knighton et al. |
| 2004/0068309 A1 | 4/2004 | Edelman |
| 2004/0068310 A1 | 4/2004 | Edelman |
| 2004/0236261 A1 | 11/2004 | McCarthy et al. |
| 2005/0131321 A1 | 6/2005 | Ravikumar |
| 2005/0143797 A1 | 6/2005 | Parish et al. |
| 2005/0187499 A1 | 8/2005 | Gillis et al. |
| 2005/0187501 A1 | 8/2005 | Ravikumar |
| 2005/0192561 A1 * | 9/2005 | Mernoe ....................... 604/890.1 |
| 2005/0222651 A1 | 10/2005 | Jung, Jr. |
| 2006/0149171 A1 | 7/2006 | Vogel et al. |
| 2007/0112401 A1 | 5/2007 | Balachandran et al. |
| 2008/0058911 A1 | 3/2008 | Parish et al. |
| 2008/0245361 A1 | 10/2008 | Brown |
| 2008/0249442 A1 | 10/2008 | Brown et al. |
| 2008/0249444 A1 | 10/2008 | Avitable et al. |
| 2008/0249559 A1 | 10/2008 | Brown et al. |
| 2009/0062701 A1 * | 3/2009 | Yannopoulos et al. ......... 601/41 |
| 2009/0069731 A1 * | 3/2009 | Parish et al. .................. 601/150 |
| 2009/0177222 A1 | 7/2009 | Brown et al. |
| 2009/0204037 A1 | 8/2009 | Ravikumar |
| 2009/0227917 A1 | 9/2009 | Nardi |
| 2009/0254160 A1 | 10/2009 | Shawver et al. |
| 2009/0312681 A1 | 12/2009 | McSpadden et al. |
| 2010/0004575 A1 | 1/2010 | Vess |
| 2010/0030306 A1 | 2/2010 | Edelman et al. |
| 2010/0076356 A1 * | 3/2010 | Biondo et al. ................. 601/149 |
| 2010/0210982 A1 | 8/2010 | Balachandran et al. |
| 2011/0022762 A1 * | 1/2011 | Waldhoff et al. ............. 710/303 |
| 2011/0077723 A1 | 3/2011 | Parish et al. |
| 2011/0082401 A1 * | 4/2011 | Iker et al. ..................... 601/152 |

* cited by examiner

SEPARABLE SYSTEM FOR APPLYING COMPRESSION AND THERMAL TREATMENT

CROSS-REFERENCE TO RELATED APPLICATION

This application claims priority to U.S. Provisional Application Ser. No. 61/342,759 filed Apr. 19, 2010, the entirety of which is incorporated herein by this reference.

FEDERALLY SPONSORED RESEARCH OR DEVELOPMENT

Not Applicable.

BACKGROUND OF THE INVENTION

The present invention relates generally to a device for applying compression and thermal treatment to a patient. The device is coupled to a therapeutic wrap that is worn by a patient. Generally, the therapeutic wraps are comprised of two fluid-tight chambers. The device is capable of filling one of the fluid-tight chambers of the wrap with a gas and may fill another fluid-tight chamber with a liquid that is varied in temperature in order to apply thermal and compression therapy to a patient. Such thermal and compression therapy is particularly suited to the treatment of patients recovering from injury or surgery as well as for the treatment and prevention of deep vein thrombosis, but may have other uses as well. The present invention offers patients the ability to utilize thermal therapy in combination with compression therapy, apply compression therapy without the thermal therapy system and maintain a record of the machine's operation.

Prior to the present invention, patients were forced to choose between purchasing or renting, on one hand, a single inseparable device that performed both compression and thermal therapy and, on the other hand, two separate devices, one for the application of compression therapy and the other for the application of thermal therapy. Each choice had significant drawbacks.

One particular drawback of the single, inseparable devices used in the application of compression and thermal therapy is their size and weight. Typically, the device used to supply the compression and thermal therapy includes a reservoir for holding a liquid, a thermal transfer system for heating and/or cooling a liquid, and a pump for pumping the liquid from the device to a wrap worn by a patient. The devices are also equipped with an air compressor for pumping a gas into a wrap worn by a patient. At least one controller is also provided in the device so that a patient may control the temperature, pressure, and duration, among other things, of the therapy. One such device is disclosed in U.S. Patent Application Publication 2008/0058911 ("the '911 application") filed on behalf of Parish et al. All of the aforementioned components, as can be seen in the '911 application, along with batteries for powering the device, add to the significant bulk of the overall device.

It is common practice for patients seeking medical attention to seek a doctor located a significant distance away from the patient's domicile. In such instances, the patient may need to travel between the doctor's locale and the patient's domicile over the time period where at least compression therapy for the treatment and prevention of deep vein thrombosis is desired. With past devices, the patient was required to travel with the entire device, which was heavy and cumbersome as a result of the reservoir, thermal transfer system, air compressor and the controller that controls the fluid pump and air compressor being contained in a single, inseparable casing. Consequently, patients had to choose between traveling with the entire device on their person (particularly difficult when air travel was involved) and missing one or more therapy sessions. Missing therapy sessions could be very serious, potentially leading to the development of a pulmonary embolism.

The utilization of two separate devices also exhibited a number of drawbacks. For example, utilizing two separate devices required either two separate battery chargers, one for the thermal device and another for the compression device, or charging the batteries of the two devices sequentially. Having only one charger subjected the patient to the risk needing to use both devices, but only being able to charge and use one device. Requiring two charges added to the expense of the systems. Additionally, there was no reliable way to keep both the thermal system and the separate air compression system together because neither device connected to the other. The lack of connection increased the possibility that a patient would, when traveling, transport only one of the two required machines, or, while at home, misplace or lose one of the two machines.

A further problem relating to prior art machines is the inability of the patient (or a technician or other person) to track the operation of the machine. Typically, a doctor will prescribe particular parameters of use for the machine which the patient is supposed to follow. For example, a doctor may prescribe a patient to use the machine to supply thermal treatment twice a day and to supply compression treatment four times a day, each for thirty minutes per treatment. However, the prior art machines lacked the ability to store data relating to the actual time the machine operated or under what parameters the machine operated (such as temperature, compressive force and duration), and thus there was no reliable way to determine whether the doctor's prescription for use had been adequately carried out by the patient.

Prior art machines also had the added drawback of control panels that were affixed to the machine. That is, the control panel of the machine could not be removed from the machine without taking apart the machine, which usually requires tools, or without breaking the machine so that once removed, the control panel no longer functioned to control the machine. Nor were any of the prior art machines provided with any type of remote control device. Consequently patients using the machine had to access to the control panel located on the machine in order to control the operation of the machine. Such access was problematic in that the machines were generally placed on the ground, while the patient would be in a chair, often times subject to limited mobility while the machine was in use. Thus patients had great difficulty in reaching the controls of the machine, and often would require the assistance of another person, such as a nurse or caregiver, to change settings on the machine during use.

SUMMARY OF THE INVENTION

The present invention solves the aforementioned problems by physically separating the overall device into two sections, a first section (thermal therapy section) and a second section (an air compressor or "DVT section", though it is not limited to the treatment of deep vein thrombosis), each of which may be connected to the other. According to the present invention, at least the DVT section is equipped with a controller and an air compressor, both of which are housed in a casing that is separable from another section that includes the thermal therapy elements (the "thermal therapy section"). The controller is capable of operating the air compressor in the DVT section without any connection to the thermal therapy section.

However, both sections may be connected together as well. In the invention described herein, the thermal therapy section is equipped with a receiving area (a dock or docking station) that accommodates the DVT section. The docking station can also be equipped with an electrical connection that connects the controller and/or batteries of the DVT section to the thermal therapy section. Placing the DVT section in the docking station can allow the controller to control the entire device and/or can allow for power transfer from the thermal therapy section to the DVT section. For example, the docked controller can control the fluid pump, the thermal transfer system and the air compressor of the DVT section and can recharge its batteries.

Furthermore, the thermal therapy section of the present invention may be equipped with a removable remote control. The remote control communicates with either or both of a controller in the thermal therapy section and the controller in the DVT section. The remote control may be in the form of a removable faceplate control panel on the thermal therapy device, it may be integrated with the DVT section, or it may be an additional remote control device that utilizes either wireless or wired communication. The faceplate may be mechanically secured to the thermal therapy section and in communication with a controller of the therapy device and thereby control various operations of the therapy device while secured, or may be removed from the thermal therapy section and used to control various aspects of the therapy device while removed.

Consequently, the patient may utilize the therapy system of the present invention in multiple configurations. For example, the DVT section can be used independently from the thermal therapy section to apply air compression therapy to a wrap. The DVT section may also be docked with the thermal therapy section such that the two sections may be used in conjunction with one another to apply both thermal therapy by pumping a thermal liquid to a wrap from the thermal therapy section as well as applying air compression therapy to a wrap from the DVT section.

A further feature of the present invention is a system to provide a reliable way to determine whether a doctor's prescription for use had been adequately carried out by the patient. According to the present invention, one or more memories for storing data relating to the operation of the machine are provided. The patient, technician or some other person may thus access the memory and review the operation of the machine to determine whether it had been operating as intended.

DETAILED DESCRIPTION OF THE PREFERRED EMBODIMENTS

Prior Art devices, such as the device disclosed in the '911 application, are generally equipped with a control panel as well as a number of ports. The ports are used to connect one or more therapy wraps to the device. Examples of suitable therapy wraps are disclosed in U.S. Pat. No. 7,198,093 issued to Elkins, U.S. Pat. No. 7,442,175 issued to Meyer et al., U.S. Pat. No. 6,352,550 issued to Gildersleeve et al., U.S. Pat. No. 5,411,541 issued to Bell et al. and U.S. patent application Ser. No. 12/798,689, filed Apr. 9, 2010, on behalf of Wilford et al, and issued as U.S. Pat. No. 8,460,224. Some ports may be used to supply and/or exchange compressed air, while other ports may be used to supply and/or exchange a thermal liquid. Typically, prior art devices like that of application '911 house within them a controller, an air compressor, a liquid pump, a reservoir, a thermal exchange system and batteries.

Figure 1A:
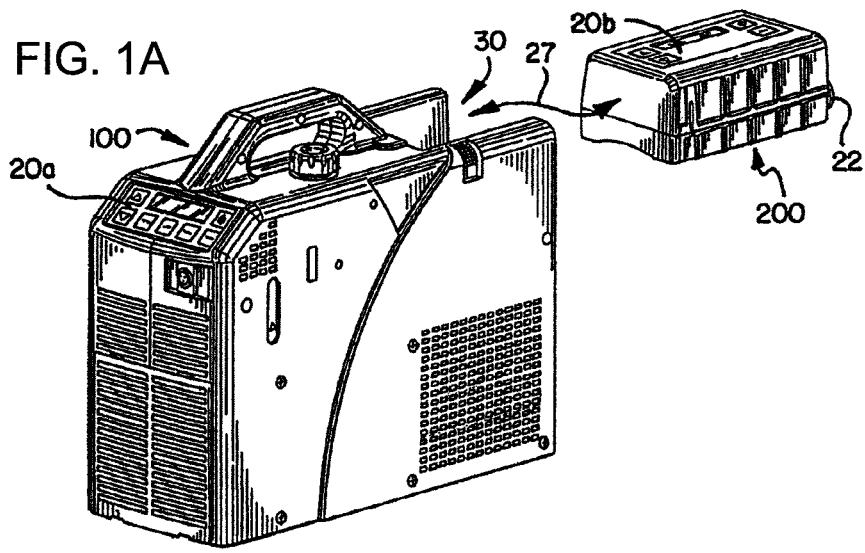
FIG. 1A is a depiction of one embodiment of the present invention, shown in a separated state and a forward facing orientation.
Figure 1B:
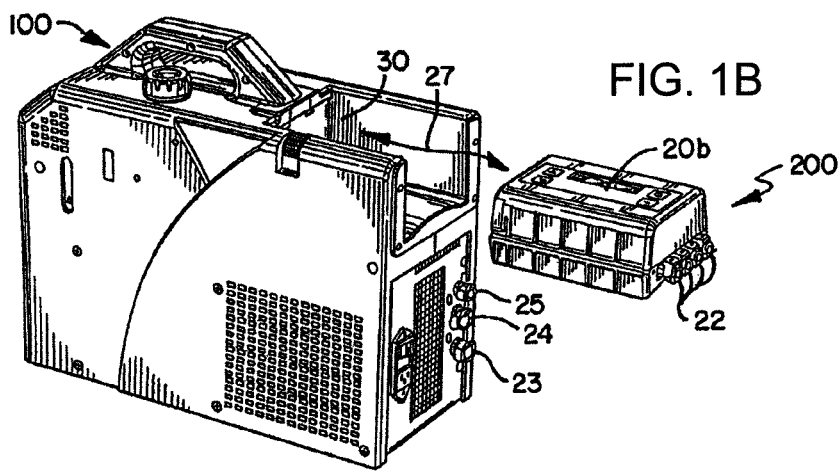
FIG. 1B is a depiction of one embodiment of the present invention, shown in a separated state and a rear facing orientation.
Figure 1C:
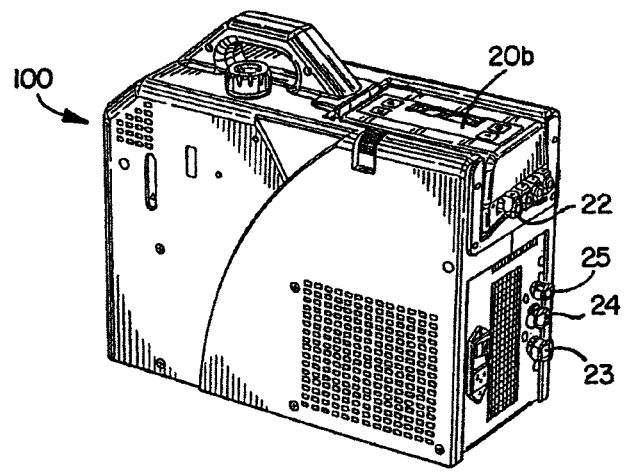
FIG. 1C is a depiction of one embodiment of the present invention, shown in a docked state and a rear facing orientation.

Throughout the specification, wherever practicable, like structures will be identified by like reference numbers. FIGS. 1A, 1B and 1C are depictions of one embodiment of the present invention. The device is made up of two sections, a first section, section 100, and a second section, section 200. Section 100 contains components necessary for applying thermal therapy. For example, it includes a reservoir, a thermal exchange system and a liquid pump and may include a first section air compressor as well. Preferably, the reservoir is oriented below any electrical components housed within section 100 such that in the event of a reservoir failure, liquid from the reservoir will not leak out and drip onto the electrical components. First section ports 23 and 24 of section 100 are adapted for supplying and/or exchanging a thermal liquid with a therapeutic wrap, and first section port 25 is adapted for supplying and/or exchanging gas with a therapeutic wrap. Preferably, an air compressor included in section 100 is adapted for supplying a range of compressive force of up to approximately 15 millimeters of mercury to a therapeutic wrap (not shown). Section 100 further includes a first section controller (not shown) and user interface first section control panel 20a. Using the control panel 20a, a user may input commands to the controller of section 100 which in turn transmits the corresponding appropriate control signals to the thermal exchange system, liquid pump and/or air compressor of section 100.

Section 200 includes elements necessary for applying compression treatment. It is equipped with a second section air compressor, and second section ports 22. The ports are adapted to supply and/or exchange air from the air compressor to a therapeutic wrap (not shown). Preferably the air compressor of section 200 is adapted for supplying a range of compressive force of up to approximately 100 millimeters of mercury. Section 200 further includes a second section controller (not shown) connected to a second section control panel user interface 20b. Utilizing the control panel 20b, a user may input commands to the controller of section 200 which in turn transmits the corresponding appropriate control signals to the air compressor of section 200. Control panels 20a and 20b may consist of a display and a series of buttons or a touch screen, or some combination thereof.

Though both sections 100 and 200 operate independently from one another, it is common for patients to utilize multiple therapeutic wraps simultaneously and thus utilize section 100 to supply thermal and/or compression treatment while simultaneously utilizing section 200 to supply additional compression treatment. To facilitate such dual usage, sections 100 and 200 may be combined together. As shown in FIGS. 1A through 1C, section 100 includes a docking station 30. Section 200 is of a size and shape corresponding to that of docking station 30. Thus, as indicated by arrow 27, section 200 may be inserted into docking station 30 (the "docked" position depicted in FIG. 1C) and withdrawn from docking station 30. Preferably, when section 200 is docked section 200 engages dock 30; that is, in the event that section 100 is caused to alter its orientation when section 200 is docked, section 200 will remain docked within docking station 30, and will not dislodge from docking station 30 simply due to the force of gravity. Section 200 may engage dock 30 by way of one or more resilient clips or snaps, pins or screws, or even simple friction. The preferred system for engaging section 200 with docking station 30 is described in further detail herein with reference to FIGS. 6 through 9. Regardless of how section 200 engages docking station 30, section 200 and docking station 30 are designed such that a user may repeatedly engage and disengage the two.

Furthermore, section 100 may also include a power transfer system, such as simple electrical contacts (not shown) within docking station 30 and on section 200, for supplying power to section 200. The power transfer system enables a transfer of power from section 100 to section 200 to recharge a battery of section 200 and/or provide operational power to section 200. Thus, docking section 200 in docking station 30 allows a patient to utilize section 200 when its battery is depleted and/or recharge the battery of section 200 for later use.

Each of sections 100 and 200 may further include one or more memories in communication with the controllers of section 100 and 200 for storing data, such as data relating to the operation of the device. A patient, technician or other person may access the memories and download the data. Preferably, the memories included in sections 100 and 200 are removable memories such as USB flash drives, secure digital (SD) memory cards, MultiMediaCards (MMC) or MS Pro memory sticks. The controllers in sections 100 and 200 transmit data corresponding to the operation of sections 100 and 200 to the memories of sections 100 and 200, respectively. When removable memories are utilized, the removable memories may be removed from the sections 100 and 200 and connected to an external device such as a computer. Thereafter, the data, such as the data corresponding to the operation of sections 100 and 200, may be downloaded from memories to the external device.

Figure 2A:
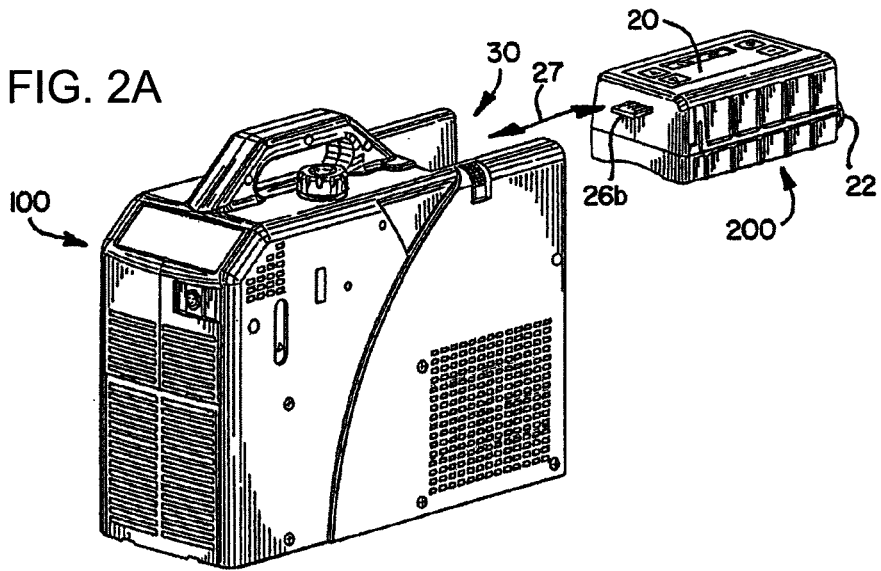
FIG. 2A is a depiction of one embodiment of the present invention, shown in a separated state and a forward facing orientation, exhibiting a single control panel.
Figure 2B:
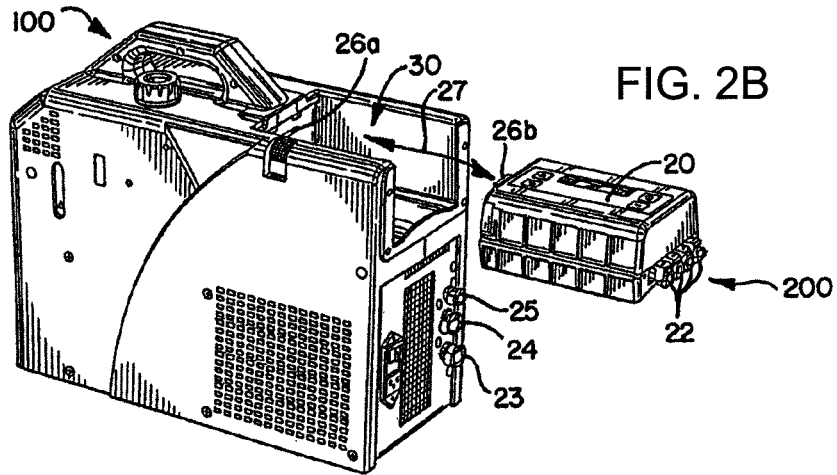
FIG. 2B is a depiction of one embodiment of the present invention, shown in a separated state and a rear facing orientation, exhibiting a single control panel.
Figure 2C:
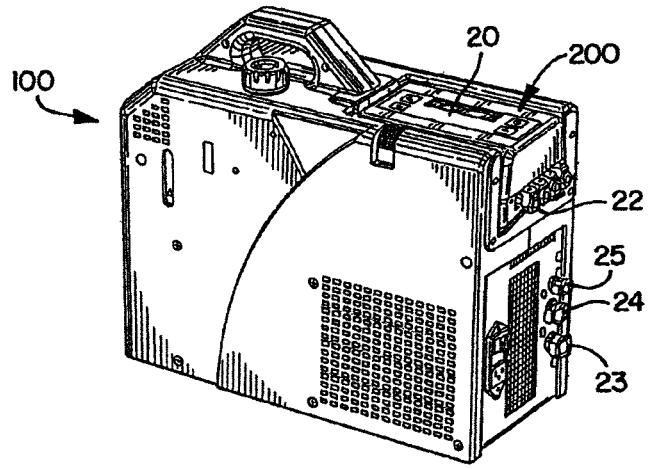
FIG. 2C is a depiction of one embodiment of the present invention, shown in a docked state and a rear facing orientation, exhibiting a single control panel.

FIGS. 2A, 2B and 2C are depictions of a further embodiment of the present invention. Again, the device is made up of two sections, section 100 and section 200. Section 100 contains components necessary for applying thermal therapy while section 200 includes components necessary for applying compression therapy. Section 100 also includes a docking station 30. However, according to the embodiment of FIGS. 2A through 2C, docking station 30 is further equipped with an electrical connection plug 26a. Electrical connection plug 26a may be one of any number of connections types suitable for the transmission of electrical signals such as a USB plug, Firewire, SATA, eSATA, SCSI or other electronic interface plugs for electrically connecting two devices. Electrical connection plug 26a may be either a male or female plug.

As described above, section 100 may also include a power transfer system, such as simple electrical contacts within docking station 30, for supplying power (as opposed to data signals) to section 200. It should be apparent, however, that where an electrical connection plug 26a is of a style that includes power transfer contacts (such as a USB connection), an additional power transfer system for supplying power is unnecessary.

In the embodiment depicted in FIGS. 2A-2C, section 200 includes a control panel 20, an electrical connection plug 26b, corresponding to the electrical connection plug 26a of section 100, and at least one port 22. In FIGS. 2A and 2B, section 200 is equipped with four ports 22, and it is contemplated that more or less ports could be used. The port or ports of section 200 are connected to the air compressor within section 200 and are adapted for the supply and/or exchange of air from the compressor to a therapeutic wrap (not shown). Control panel 20 may consist of a display and a series of buttons or a touch screen, or some combination thereof. Section 200 also includes an air compressor (not shown) and a battery (not shown) for supplying power.

Section 200 further includes at least one controller (not shown) which is electrically connected to the control panel, the air compressor, the battery and to plug 26b. The controller is responsible for controlling the air compressor of section 200. In the embodiment depicted in FIGS. 2A through 2C, section 100 does not include any control panel. Instead, all of the elements of section 100 are controlled utilizing control panel 20 included in section 200. Thus, the controller of section 200 controls not only the air compressor of section 200, but also, when section 200 is docked with section 100 (as will be explained below), the liquid pump, air compressor and thermal exchange system of section 100, each of which are electrically connected to the plug 26a.

As shown by arrow 27 in FIGS. 2A and 2B, section 200 may be inserted into docking station 30. Section 200 slides into the cavity of docking station 30 and plugs 26a and 26b are connected together. FIG. 2C is a graphical depiction of section 100 and section 200 docked together. When section 100 and section 200 are docked together, control panel 20 is electrically connected to the electrical components of section 200 as well as to the electrical components of section 100 by virtue of plugs 26a and 26b being connected together.

Where multiple controllers are utilized, one controller, for example, may be dedicated to the control of the air compressor of section 200 and one or more controllers may be dedicated to the control of the liquid pump and thermal exchange system of section 100. Where multiple controllers are utilized, the controller for controlling the air compressor of section 200 is located within section 200, but the controller or controllers for controlling the liquid pump, thermal exchange system and/or other components of section 100 may be located within either section 100 or section 200.

Because section 200 is equipped with an air compressor, a control panel and at least one controller that controls the air compressor, it is capable of operating independently of section 100. The control panel 20 may be used by a patient to input commands to the controller which then controls the operation of the air compressor of section 200 to apply compression therapy to a therapeutic wrap connected to the ports 22. Such a configuration is particularly advantageous where a patient is traveling and only compression therapy is desired because the smaller section 200 can easily be transported by the patient and the bulky section 100 may be stowed or left behind.

As indicated above, the embodiment depicted in FIGS. 2A through 2C may include multiple controllers. One or more of those controllers may also communicate with at lest one memory. Preferably the memory is removable. Data, such as data relating to the operation of sections 100 and 200, may be stored on the memory and subsequently downloaded to an external device by a patient, technician or other person.

Figure 3A:
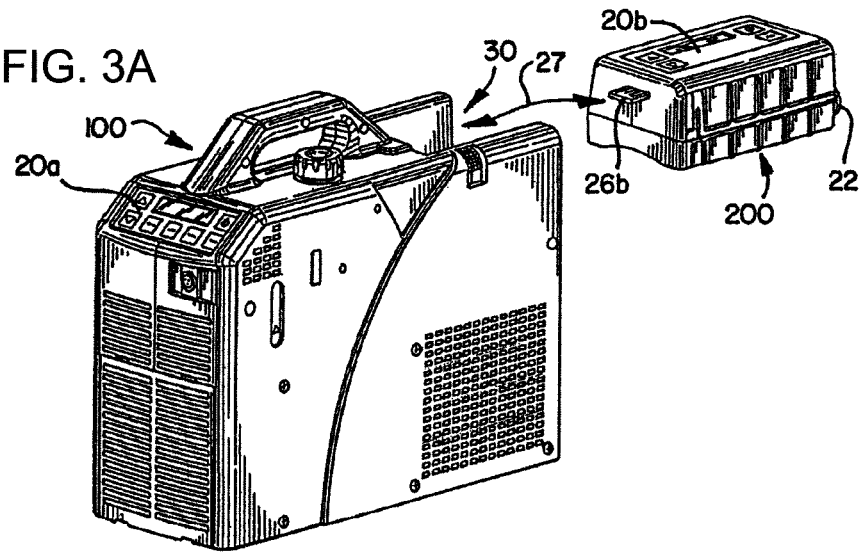
FIG. 3A is a depiction of one embodiment of the present invention, shown in a separated state and a forward facing orientation, exhibiting multiple control panels.
Figure 3B:
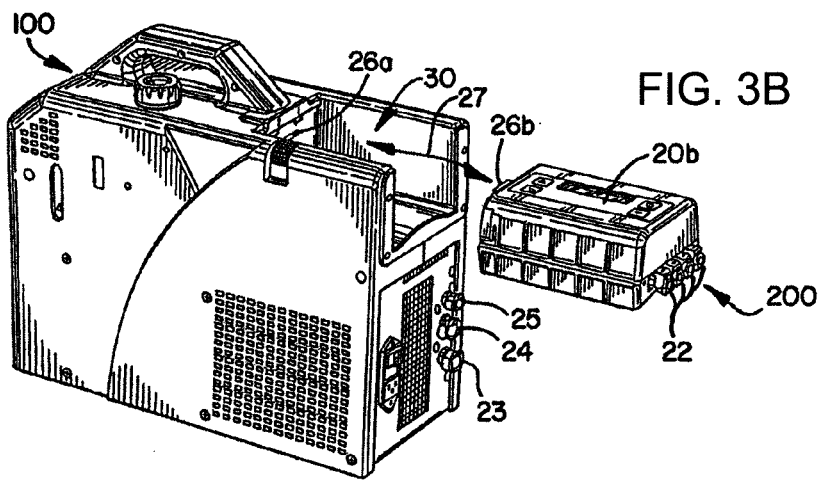
FIG. 3B is a depiction of one embodiment of the present invention, shown in a separated state and a rear facing orientation, exhibiting multiple control panels.
Figure 3C:
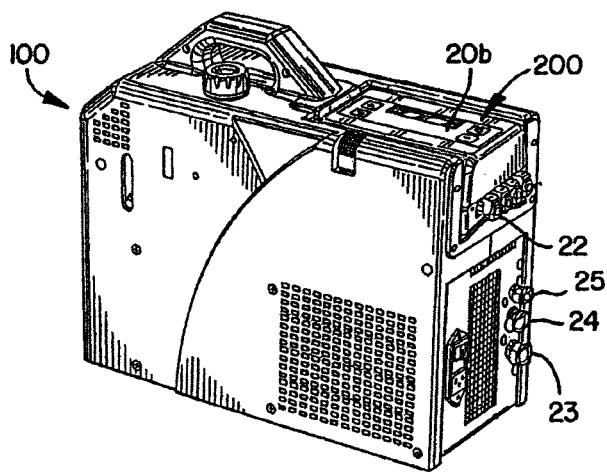
FIG. 3C is a depiction of one embodiment of the present invention, shown in a docked state and a rear facing orientation, exhibiting multiple control panels.

In FIGS. 3A through 3C another embodiment of the present invention is depicted where both sections 100 and 200 are supplied with control panels, identified by numerals 20a and 20b, respectively. As with the embodiment described in connection with FIGS. 1A through 1C, control panels 20a and 20b may consist of a display and a series of buttons or a touch screen, or some combination thereof and each of sections 100 and 200 can work independently from one another.

According to the embodiment of FIGS. 3A through 3C, control panel 20a may be electrically connected to one or more controllers that control the liquid pump, air compressor and thermal exchange system of section 100. Similarly, control panel 20b may be electrically connected to at least one controller that controls the air compressor of section 200. Thus, when section 100 and section 200 are separated from each other, a user may use control panel 20a to control the application of thermal therapy, and/or may use control panel 20b to control the application of compression therapy.

However, as indicated in FIG. 3C, section 200 may also be docked with section 100, such that the control panel 20b is electrically connected to the electrical components of both section 200 and section 100, and/or the control panel 20a is electrically connected to the electrical components of section 100 and section 200. With both the controller of section 100 and the controller of section 200 being connected to both control panels 20a and 20b, control panel 20a and/or control panel 20b could be used by a patient to control the application of both thermal therapy and/or compression therapy. However, it is preferred that docking section 200 with section 100 causes the controller of section 100 to override the controller of section 200 such that only control panel 20a of section 100 may be used to control the application of thermal therapy and compression therapy from both sections 100 and 200 while the two sections remain docked. Such a configuration would only require that control panel 20a be equipped with appropriate user interface for controlling both thermal therapy and compression therapy for all ports where control panel 20b would only require a user interface for controlling compression therapy from ports 22. It is of course understood that the controller of section 200 could be configured to override the controller of section 100, and that control panel 20b could be equipped with the appropriate interface to control both thermal therapy and compression therapy from all ports.

In the embodiment according to FIGS. 3A through 3C, section 100 may also include a power transfer system, such as simple electrical contacts within docking station 30, for supplying power (as opposed to data signals) to section 200. It should be apparent, however, that where an electrical connection plug 26a is of a style that includes power transfer contacts (such as a USB connection), an additional power transfer system for supplying power is unnecessary.

Figure 4A:
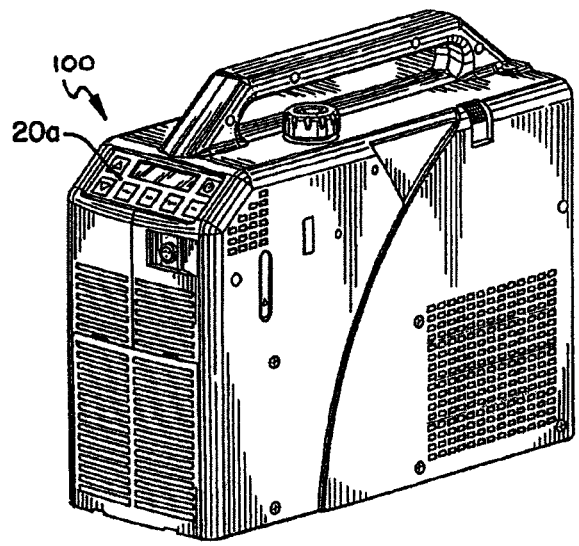
FIG. 4A is a depiction of one embodiment of the present invention, shown in a docked state and a forward facing orientation, exhibiting a covered dock.
Figure 4B:
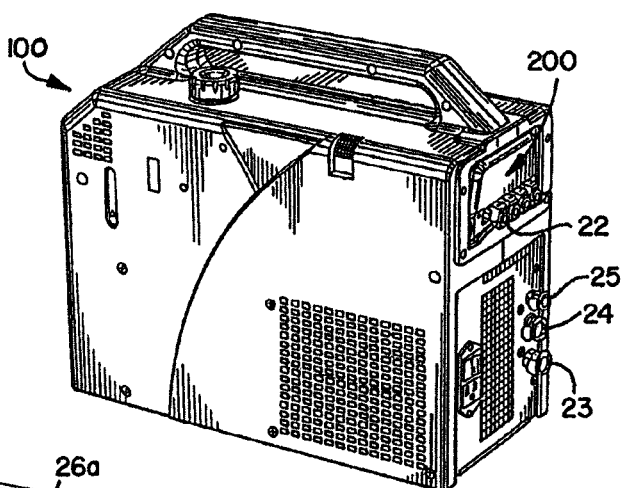
FIG. 4B is a depiction of one embodiment of the present invention, shown in a docked state and a rear facing orientation, exhibiting a covered dock.
Figure 4C:
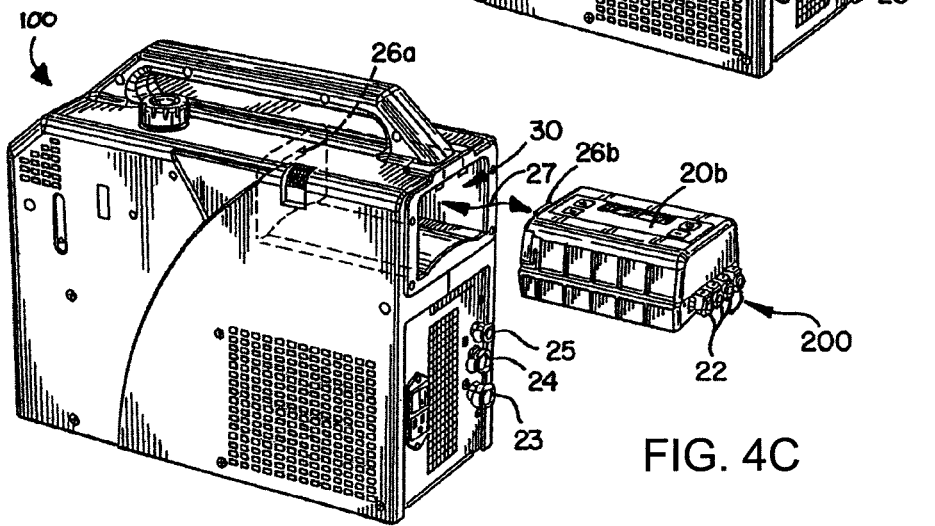
FIG. 4C is a depiction of one embodiment of the present invention, shown in a separated state and a rear facing orientation, exhibiting a covered dock.

FIGS. 4A, 4B and 4C depict another embodiment of the present invention. Section 100, shown in FIGS. 4A, 4B and 4C, is constructed similar to that described above in relation to FIGS. 3A and 3B, the primary difference being the style of dock. As shown in FIG. 3A, the cavity of docking station 30 allows the control panel 20b to remain exposed when section 200 and section 100 are docked. However, as shown in FIGS. 4A and 4B, when section 200 is docked with section 100, the control panel 20b is covered by section 100. Thus, the control panel 20b is obscured and users are prevented from inputting commands using the control panel 20b. It is not necessary that the control panel 20b be completely covered, but rather that it be obscured enough to prevent a user from inputting all of the control commands necessary to operate the present invention.

According to the embodiment of FIGS. 4A, 4B and 4C therefore, when sections 100 and 200 are docked, only control panel 20a may be used to control the operation of the liquid pump, thermal exchange system and air compressors. The benefit of the configuration depicted in FIGS. 4A, 4B and 4C is that there is no confusion on the part of the patient which control panel should be used when section 100 and section 200 are docked.

Figure 5A:
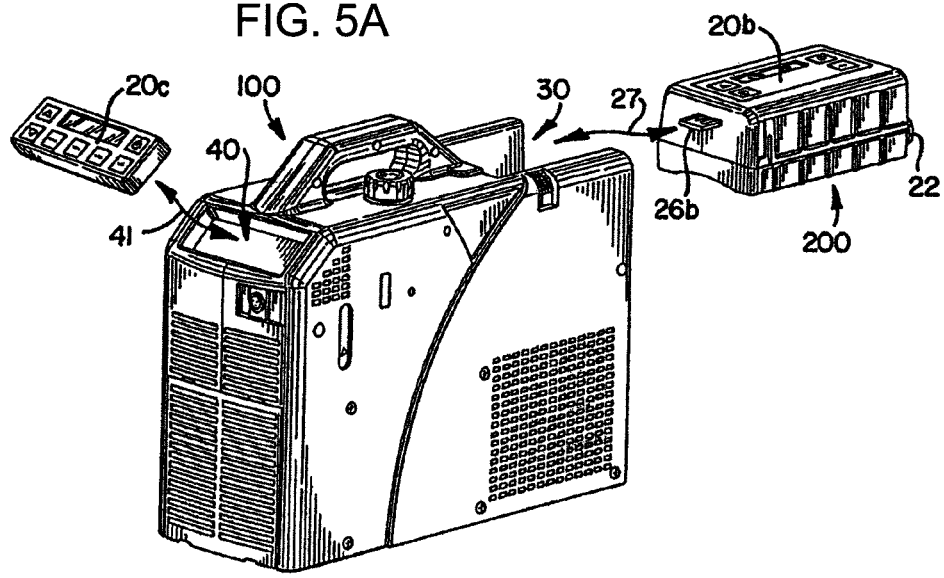
FIG. 5A is a depiction of an embodiment of the present invention having a removable faceplate.

FIG. 5A is a depiction of an alternate embodiment of the present invention which utilizes a removable faceplate remote control, faceplate 20c. Faceplate 20c includes all of the controls of 20a described previously. As shown in FIG. 5A, section 100 includes a faceplate dock 40. Faceplate 20c is of a size and shape corresponding to that of faceplate dock 40. Thus, as indicated by arrow 41, faceplate 20c may be inserted into faceplate dock 40 (the "docked" position) and withdrawn from faceplate dock 40. When faceplate 20c is docked, faceplate 20c engages faceplate dock 40. Thus, in the event that section 100 is caused to alter its orientation when faceplate 20c is docked, faceplate 20c will remain docked with faceplate dock 40, and will not dislodge from faceplate dock 40 simply due to the force of gravity. Faceplate 20c may engage faceplate dock 40 by way of one or more resilient clips or snaps, pins or screws, or even simple friction.

Regardless of how faceplate 20c engages faceplate dock 40, faceplate 20c and faceplate dock 40 are designed such that a user may repeatedly engage and disengage the two. It is preferred that when faceplate 20c is docked, it is also electrically connected to at least one controller in section 100. Electrically connecting faceplate 20c to at least one controller in section 100 allows faceplate 20c to communicate with the controller or controllers of section 100 in the same way as control panel 20a does in the aforementioned embodiments. Electrically connecting faceplate 20c to section 100 also provides a system by which section 100 may transfer power to faceplate 20c.

Once removed from section 100, as shown in FIGS. 5A, it is contemplated that the faceplate 20c may be used to control various aspects of section 100 and/or section 200. Faceplate 20c thus includes a signal emitter (not shown) and section 100 includes a signal receiver (not shown). In use, a patient, for example, actuates inputs, such as buttons or a touch screen, on faceplate 20c causing faceplate 20c to emit a signal which is received by the receiver in section 100 and communicated to one or more controllers (not shown) in section 100. When section 200 is docked as shown, for example, in FIGS. 3C and 4B, the signal received by the receiver in section 100, or a signal generated by a controller in section 100 in response to the signal received by the receiver in section 100 may be transmitted to section 200 and used to control elements of section 200. Alternately, section 200 may be equipped with its own separate receiver for receiving signals emitted from faceplate 20c and may receive signals and control section 200 either while docked or not docked. It should be appreciated that, section 200 may include a signal emitter and be used as a remote control, in which case control panel 20b would contain all of the controls necessary for controlling the operation of section 100, as described with reference to FIGS. 2A through 2C.

It is contemplated that the receiver in section 100 that receives the signals from faceplate 20c may be a separate component connected to the one or more controllers by wiring, or may be integrated with at least one of the controllers of section 100. Likewise if section 200 is equipped with a receiver, the receiver of section 200 may be a separate component connected to the one or more controllers in section 200 by wiring, or may be integrated with at least one of the controllers of section 200. Preferably, each receiver and the signals emitted by faceplate 20c are each coded and match such that the faceplate 20c only controls one therapy device having the matching receiver or receivers. The receipt, generation and emission of coded signals for wireless communication between electronics is well known in the art of wireless communication and is particularly important for devices used in hospitals to prevent unwanted cross communication.

It should be appreciated that, in an embodiment utilizing section 200 as a remote control, section 200 is equipped with a signal emitter and section 100 includes a signal receiver as described above. Once removed from dock 30, actuation of the control panel 20b on section 200 causes the signal emitter to emit a signal, preferably coded, that is received by a receiver in section 100. One or more controllers utilize the signal received from section 200 to execute control functions and control the operation of section 100.

Figure 5B:
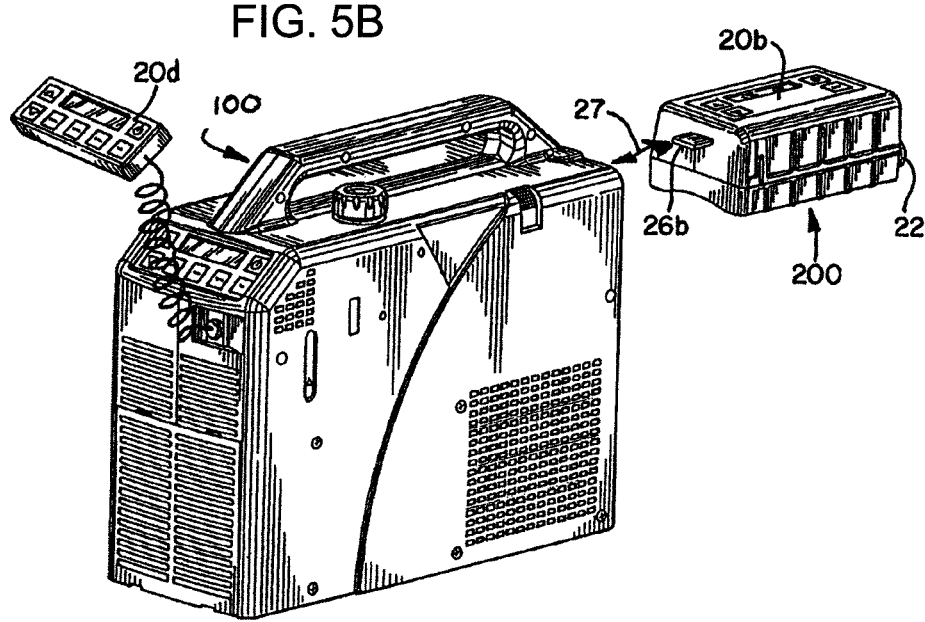
FIG. 5B is a depiction of an embodiment of the present invention having an additional remote control

In a further embodiment, shown in FIG. 5B, section 100 may be equipped with a separate remote control 20d. The remote control may communicate with sections 100 and/or 200 either wirelessly or by wire to section 100. In either case, when activated by a user, the remote control 20d emits a signal that is received by the controller of section 100 and/or the controller of section 200. In embodiments utilizing a wireless remote control 20d, it should be appreciated that, at least section 100 is equipped with a signal receiver that communicates with the controller of section 100. Additionally, section 200 may include a signal receiver as described above. Operation of the remote control 20d causes the signal emitter of the remote control 20d to emit a signal, preferably coded, that is received by a receiver in section 100. One or more controllers utilize the signal received to execute control functions and control the operation of section 100 and/or section 200.

Figure 6:
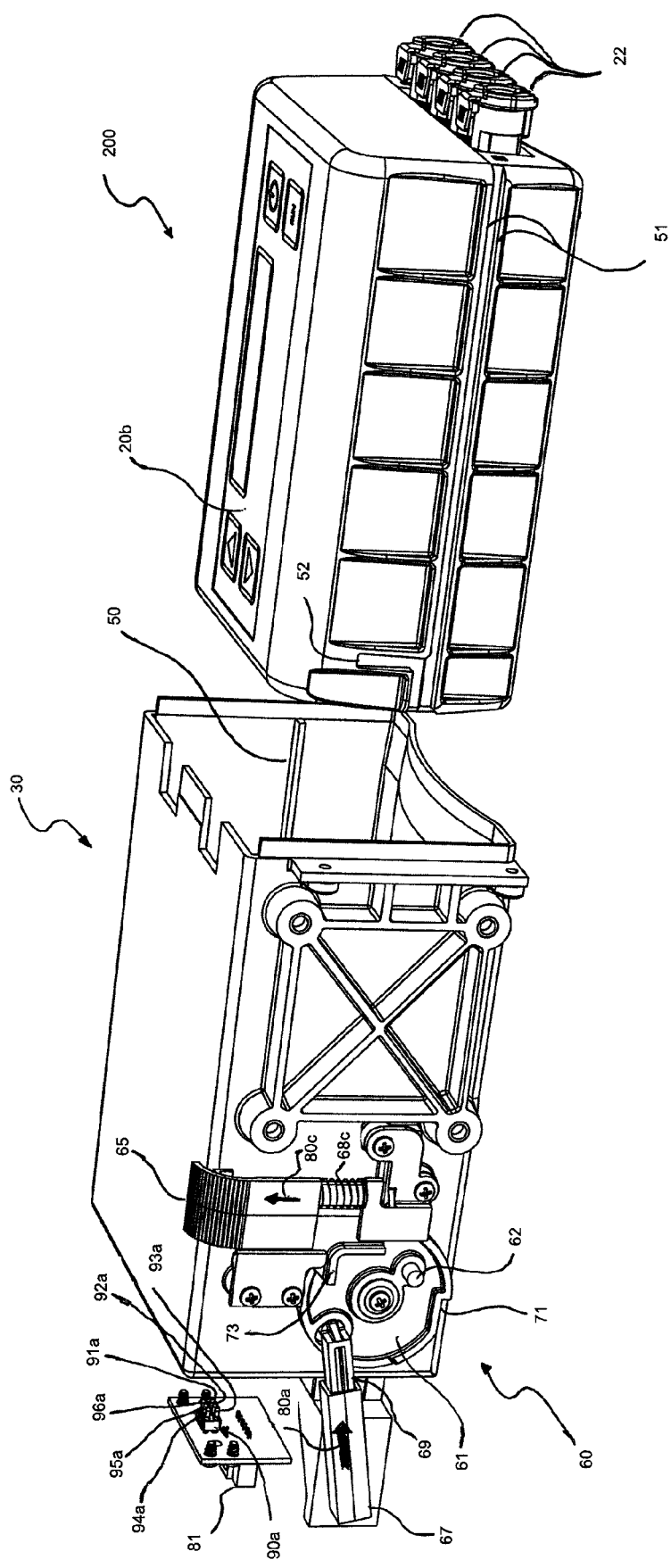
FIG. 6 is a depiction of the present invention having the exterior of the structure of the thermal transfer section removed to show the docking station of a thermal transfer section and a releasable lock prior to insertion of a DVT section.

Referring now to FIG. 6, preferably, docking station 30 of section 100 (not shown) and section 200 further includes one or more rails 50 and rail guides 51 respectively. In the embodiment depicted, the rails 50 of section 100 fit within the rail guides 51 of section 200 such that section 200 slides in an out of the docking station 30 along the rails 50. Section 200 also includes additional groove 52 extending upward from the rail guides 51. Section 100 includes a resilient clip, the preferred structure and operation of which is described in further detail below. In general, when section 200 is inserted into docking station 30, the rail guides 51 slide along rails 50 until it reaches the docked position.

When section 200 is in the docked position, the resilient clip will engage section 200 and prevent section 200 from being withdrawn from docking station 30. To remove section 200 after placing it in docked position, the resilient clip must be disengaged. Actuation of a release, such as a button or switch, located on the exterior of section 200 releases the resilient clip, thereby allowing section 200 to be removed from station 30.

The preferred resilient clip is a releasable lock, which will now be described with reference to FIGS. 6-9. According to the preferred embodiment, a releasable lock 60 is mounted to structural elements of section 100, such as the structure surrounding the cavity of the docking station 30. For explanatory purposes, the overall structure of section 100 is not shown in FIGS. 6-9, and the structure surrounding the cavity of the docking station 30 is not shown in FIGS. 7-9. Releasable lock 60 includes a wheel 61 having a lock surface 71, an exterior eccentrically mounted pin 62, an interior eccentrically mounted pin 63, a lever arm 64, a button 65 and a pawl 66. The lever arm 64 includes a case 67 pivotally mounted to a structure of section 100. Case 67 holds a resilient material 68a, such as a spring, and allows for a piston 69 to travel up and down its length. Piston 69 is pivotally mounted to wheel 61 and biased in the direction of arrow 80a by resilient material 68a. Similarly, pawl 66 is biased in the direction of arrow 80b by resilient material 68b while button 65 is biased in the direction of arrow 80c by resilient material 68c.

As discussed above, when section 200 is inserted into docking cavity 30, it slides along rails 50. As section 200 approaches the docked position, preferably within the final one inch of the docked position, pin 63 begins to engage groove 52. As section 200 moves further into the docking station, pin 63 traverses groove 52 and wheel 71 is forced in the counter clockwise direction. Movement of the wheel in the counter clockwise direction causes piston 69 to compress resilient material 68a, thereby building potential energy in resilient material 68a. Continuing to push section 200 into the docking station forces the lever arm 64 past the neutral (nine o'clock) position. Once the lever arm 64 is past the neutral position, the potential energy in the resilient material 68a is released, the piston 69 is forced in the direction of arrow 80a, the wheel is forced to rotate further in the counter clockwise direction, pin 63 fully engages groove 52 and pawl 66 (biased in the direction of arrow 80b by resilient material 68b) engages the lock surface 71. As shown in FIGS. 7-10, lock surface 71 is substantially "L" shaped, and pawl 66 includes a substantially squared end that engages lock surface 71, preventing wheel 61 from traveling in the clockwise direction while pawl 66 and lock surface 71 are engaged. It should be appreciated by those of skill in the art that most any shape of lock surface and corresponding pawl end shape could be utilized. With the pin 63 engaged with groove 52 and pawl 66 engaged with lock surface 71, section 200 is locked in the docked position.

To release the releasable lock 60 and enable the removal of section 200 from the docking station, button 65 is depressed. Depressing button 65 causes surface 72 to contact pawl 66, push pawl 66 in a direction opposite that of arrow 80b and disengage pawl 66 from lock surface 71 thereby permitting wheel 61 to move in the clockwise direction. Depressing button 75 also causes bracket 73 to apply pressure to pin 62, forcing pin 62 and wheel 61 to move in the clockwise direction. Moving pin 62 from the essentially three o'clock position that it maintains while section 200 is in the docked position in the clockwise direction forces piston 69 to likewise move in the clockwise direction, thereby compressing resilient material 68a and building potential energy in resilient material 68a. As button 65 continues to be depressed, piston 69 passes the neutral position, the potential energy stored in resilient material 68a is released, piston 69 forces wheel 61 further in the clockwise direction which in turn causes pin 63 to apply pressure to groove 52 thereby disengaging section 200 from the docking station. Preferably, sufficient pressure is applied by pin 63 to groove 52 to eject section 200 by approximately one inch, freeing section 200 from the releasable lock 60. Once disengaged, section 200 may be freely slid out of docking station 200.

Figure 7:
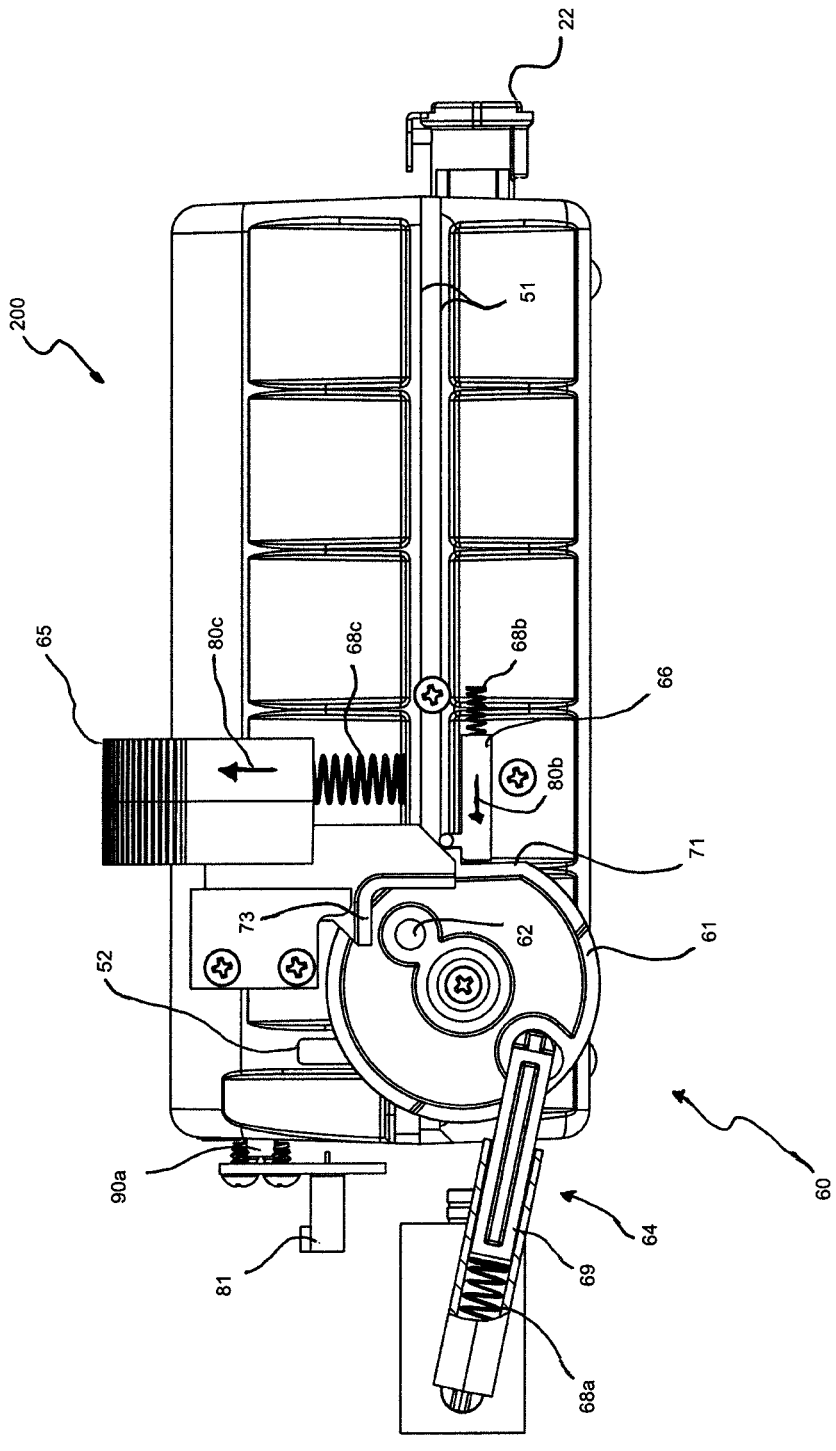
FIG. 7 is a depiction of the present invention having the exterior of the structure of the thermal transfer section removed to show the electrical contacts of a thermal transfer section and a releasable lock in addition to the insertion of a DVT section in the docked position.
Figure 8:
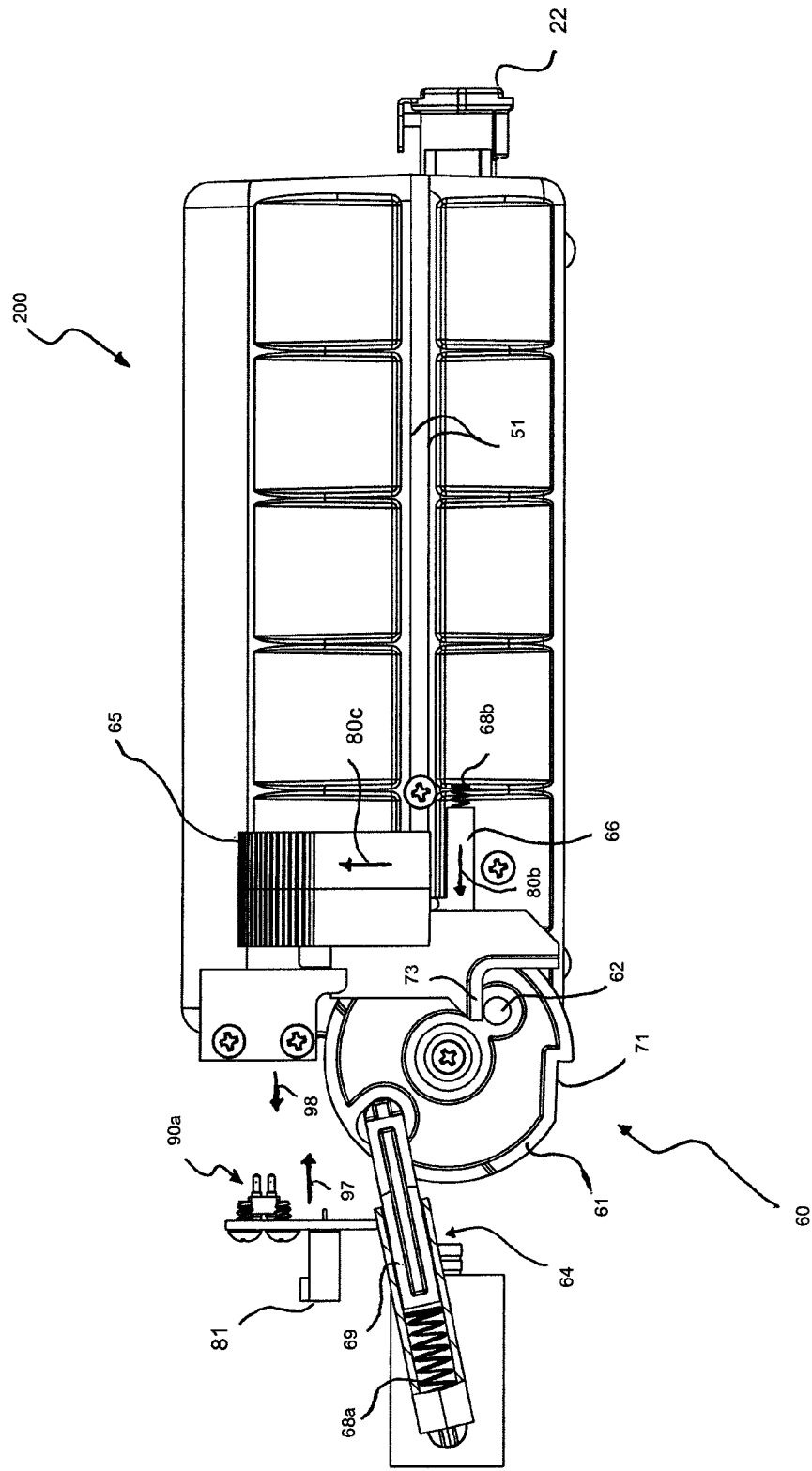
FIG. 8 is a depiction of the present invention having the exterior of the structure of the thermal transfer section removed to show the electrical contacts of a thermal transfer section and disengagement of a releasable lock to remove of a DVT section.
Figure 9:
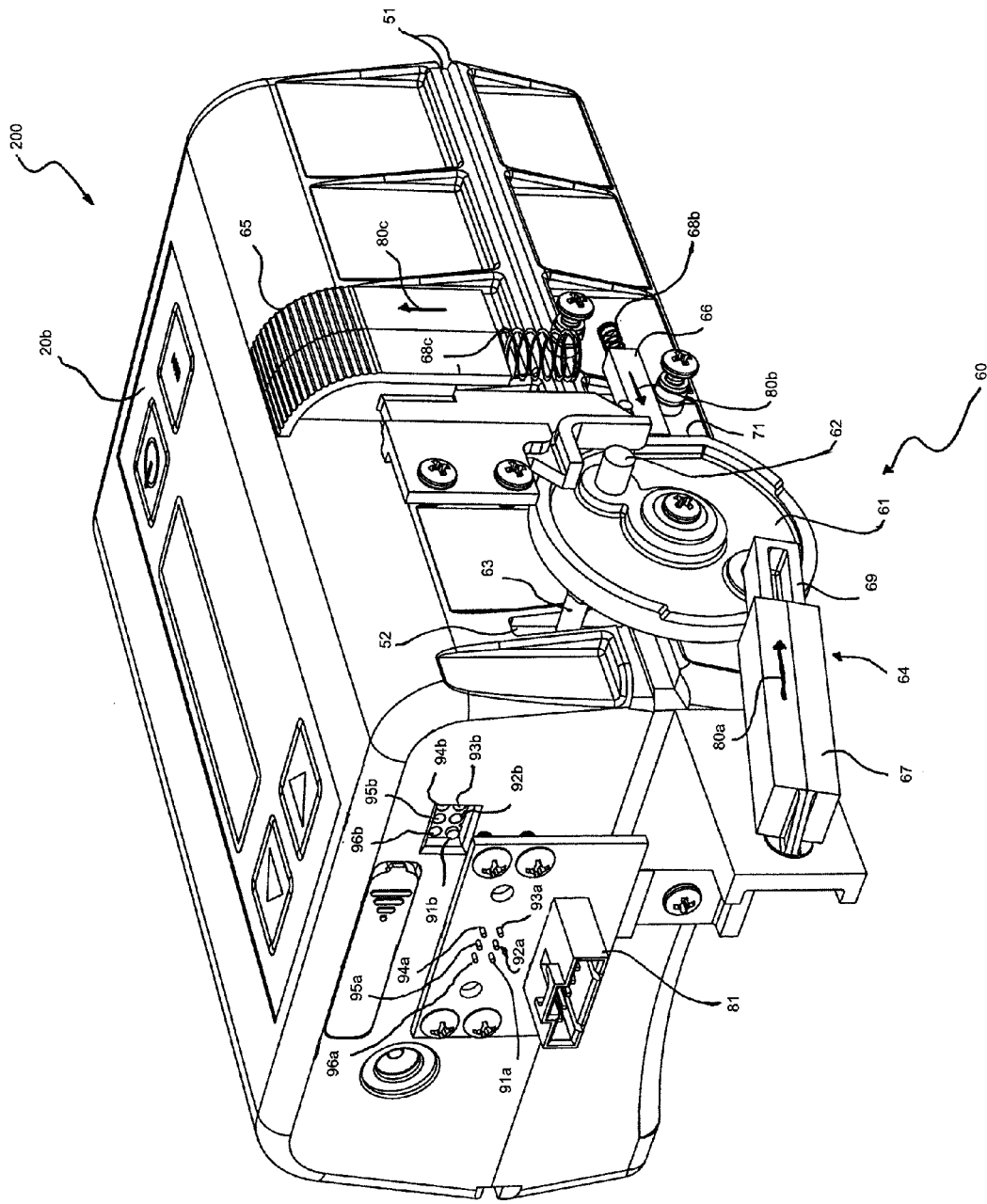
FIG. 9 is a depiction of the present invention having the exterior of the structure of the thermal transfer unit removed to show the electrical contacts of a thermal transfer section and of a DVT section.

In addition to securing section 200 in docking station 30, engaging the releasable lock 60 brings section 200 into electrical contact with section 100. As discussed above with respect to FIGS. 3A-3C, sections 100 and 200 may include respective electrical contact plugs such as 26a and 26b. As depicted in FIGS. 7 through 9, in the preferred embodiment, section 100 includes a board having electrical contact 90a while section 200 includes corresponding electrical contact 90b. Electrical contact 90a is connected to plug 81 which is in turn connected to a controller of section 100 through wiring (not shown). Preferably the contacts are utilized to transfer both power and data between section 100 and section 200. Electrical contact 90a includes multiple pins 91a, 92a, 93a, 94a, 95a and 96a. It should be appreciated that although six pins are shown, any number of pins could be utilized. When section 200 is docked with section 100, electrical contacts 90a and 90b are in electrical communication with each other.

Referring now to FIG. 10, the preferred structure of the electrical contacts will be explained. As shown, section 200 includes electrical contact 90b. 90b multiple electrical contact pads 91b, 92b, 93b, 94b, 95b and 96b corresponding to the pins 91a, 92a, 93a, 94a, 95a and 96a of electrical contact 90a. In the preferred embodiment either the pins or contact pads or both are reliantly biased to extend outwardly. That is, the pins are resiliently biased to extend in the direction of arrow 97 while the contact pads are resiliently biased to extend in the direction of arrow 98. Furthermore, it is preferred that one pin or one contact pad exhibits greater dimensions than all other respective pins and contact pads such that the greater dimensions cause one pin and one contact pad to establish a first electrical connection, which allows for electrical communication between the contact pad and pin, prior to any other pin or contact pad.

For example, as shown in FIG. 10, contact pad 91b is longer than each of contact pads 92b, 93b, 94b, 95b and 96b. Thus, when section 200 is docked with section 100, contact pad 91b establishes an electrical connection with corresponding pin 91a before any other contact pad or pin establish an electrical connection. Also, due to the resilient biasing, pin 91a and contact pad 91b will likewise be the last pin and contact pad to break their electrical connection when section 200 is undocked and separated from section 100. Preferably the electrical connection between 91a and 91b is the ground connection between section 200 and section 100. According to the preferred embodiment just described, when section 200 is docked and undocked with section 100, a ground connection will be established first and broken last thereby helping to prevent unwanted electrical surges and communications between sections 100 and 200 that may damage the controls of either section.

It should be appreciated that each of the embodiments described herein may include one or more memories for storing data, such as data relating to the operation of the various sections 100 and 200 respectively. Although the present invention has been described in terms of the preferred embodiments, it is to be understood that such disclosure is not intended to be limiting. Various alterations and modifications will be readily apparent to those of skill in the art. Accordingly, it is intended that the appended claims be interpreted as covering all alterations and modifications as fall within the spirit and scope of the invention.

What is claimed is:

1. A compression and thermal application device comprising:
 a first section including a reservoir a liquid pump, a thermal exchange system, at least one port in fluid communication with said reservoir, and a first electrical contact;
 a second section, physically separate from said first section, including an air compressor, at least one port in fluid communication with said air compressor, one or more second section controllers that control the operation of the air compressor, and a second electrical contact;
 wherein said first section further includes a dock, said dock defining a cavity having an opening that accommodates said second section and wherein said first electrical contact is located within said cavity; said first electrical contact and said second electrical contact being oriented such that when said second section is docked in said dock of said first section, said first electrical contact and said second electrical contact are in electrical communication; and
 wherein said first section further includes
 a pawl,
 a wheel having a lock surface, an exterior eccentrically mounted pin, and an interior eccentrically mounted pin that extends into said dock,
 a lever arm having a case connected to said first section, a resilient material contained within said case, and a piston having a first end that slides within said case and is biased by said resilient material in an outward direction, said piston further including a distal end connected to said wheel;
 wherein said at least one port of said second section is located on said second section such that when said second section is docked, said at least one port is exposed and accessible through said cavity; and
 wherein insertion of said second section into said dock causes said interior eccentrically mounted pin to contact a portion of said second section causing said wheel to rotate and wherein the rotation of said wheel as a result of the insertion of said second section into said dock causes said piston to apply a force to said resilient material and build potential energy in said resilient material such that when said lever arm passes a neutral position, potential energy in said resilient material is released resulting in further rotation of said wheel and further movement of said interior eccentrically mounted pin such that said pin transfers a force to said second section thereby further inserting said second section into said dock;

wherein at the neutral position, said first electrical contact and said second electrical contact do not physically touch; and wherein releasing the potential energy in said resilient material provides all the force necessary to move said second section and to force said first electrical contact to physically touch said second electrical contact.

2. The compression and thermal application device as in claim 1 further comprising:
one or more first section controllers contained within said first section and a first section control panel on said first section which is in electrical communication with at least one of said one or more first section controllers, wherein said one or more first section controllers control the operation of said liquid pump and said thermal exchange system;
a second section control panel on said second section which is in electrical communication with at least one of said one or more second section controllers;
wherein said first section control panel send electrical signals to at least one of said first section controllers and wherein said first section control panel sends control signals to at least one of said second section controllers through said first electrical contact and said second electrical contact.

3. The compression and thermal application device as set forth in claim 1 further comprising:
one or more memories physically connected to said first section or said second section and in electrical communication with any of said one or more controllers, at least one of said memories being adapted to record data respecting the actual operation of any of said one or more controllers, said thermal transfer system, said liquid pump or said air compressor.

4. The compression and thermal application device as set forth in claim 3 wherein
at least one of said one or more memories that is adapted to record data respecting the actual operation of any of said one or more controllers, said thermal transfer system, said liquid pump or said air compressor is a removable memory.

5. The compression and thermal application device as set forth in claim 1 wherein:
said first electrical contact and said second electrical contact each include a plurality of individual contacts and wherein one individual contact of the plurality of individual contacts of either the first electrical contact or the second electrical contact is a unique contact which has a dimension greater than the corresponding dimension of each of the other individual contacts of the electrical contact that the unique contact is included with such that as said first electrical contact and said second electrical contact are disconnected, a final connection between said first electrical contact and said second electrical contact occurs between said unique contact and at least one other individual contact.

6. The compression and thermal application device as set forth in claim 1 wherein:
said first electrical contact and said second electrical contact each include a plurality of individual contacts and wherein one individual contact of the plurality of individual contacts of either the first electrical contact or the second electrical contact is a unique contact which has a dimension greater than the corresponding dimension of each of the other individual contacts of the electrical contact that the unique contact is included with and wherein at least one individual contact included on the electrical contact that does not include said unique contact is a resiliently biased individual contact that is resiliently biased in a direction toward said unique contact when said second section is docked with said first section such that as said first electrical contact and said second electrical contact are disconnected, a final connection between said first electrical contact and said second electrical contact occurs between said unique contact and said at least one resiliently biased individual contact.

7. The compression and thermal application device as set forth in claim 1 wherein
one of said dock and said second section further includes at least one rail and the other of said dock and said second section further includes at least one guide that accommodates said rail such that said rail slides within said guide and said guide facilitates the proper alignment of said second section within said dock.

8. A compression and thermal application device comprising:
a first section including a reservoir, a liquid pump, a thermal exchange system, a first section air compressor, at least one port in fluid communication with said reservoir, at least one port in fluid communication with said first section air compressor, one or more first section controllers and a first control panel in electrical communication with said on or more first section controllers;
a second section, physically separate from said first section, including an air compressor, at least one port in fluid communication with said air compressor, one or more second section controllers, and a second control panel in electrical communication with at least one of said second section controllers;
wherein said first section further includes:
a dock, said dock defining a cavity having an opening that accommodates said second section and wherein said at least one port of said second section is located on said second section such that when said second section is docked, said at least one port is exposed and accessible through said cavity;
a pawl;
a wheel having a lock surface, an exterior eccentrically mounted pin, and interior eccentrically mounted pin that extends into said dock;
a lever arm having a case connected to said first section, a resilient material contained within said case, and a piston having a first end that slides within said case and is biased by said resilient material in an outward direction, said piston further including a distal end connected to said wheel;
a spring connected to said pawl wherein said spring biases said pawl toward said wheel; and
a movable bracket connected to said first section;
wherein movement of said bracket toward said external eccentrically mounted pin results in contact between said bracket and said external eccentrically mounted pin thereby rotating said wheel and causing said piston to depress said resilient material, and wherein movement of said bracket toward said external eccentrically mounted pin also results in contact between said bracket and said pawl causing said pawl to cease contact with the lock surface of said wheel, and wherein when said second section is inserted into said dock, a portion of said second section contacts said interior eccentrically mounted pin causing said interior eccentrically mounted pin to rotate said wheel and bring said lock surface into contact with said pawl.

9. The compression and thermal application device as in claim 8 further comprising:
said first section having a first electrical contact and a dock, said dock defining a cavity having an opening that accommodates said second section, said first electrical contact being located within said cavity and wherein said first control panel is in electrical communication with said first electrical contact;
said second section having a second electrical contact wherein at least one of said one or more second section controllers is in electrical communication with said second electrical contact;
wherein said first electrical contact and said second electrical contact are oriented such that when said second section is docked in said dock of said first section, said first electrical contact and said second electrical contact are in electrical communication; and
wherein said first control panel and said one or more first section controllers operate to control said liquid pump, thermal exchange system and first section air compressor when said second section is not docked.

10. The compression and thermal application device as set forth in claim 8 further comprising:
at one or more memories physically connected to said first section or said second section and in electrical communication with any of said one or more controllers, at least one of said memories being adapted to record data respecting the actual operation of any of said one or more controllers, said thermal transfer system, said liquid pump or said air compressor.

11. The compression and thermal application device as set forth in claim 1 wherein when said second section is docked, said at least one port is protrudes from said cavity.

12. The compression and thermal application device as set forth in claim 8 wherein when said second section is docked, said at least one port is protrudes from said cavity.

13. The compression and thermal application device as set forth in claim 1 further comprising:
at least one removable memory physically connected to said first section and adapted to record data respecting the actual operation of one or more of said one or more first section controllers, said liquid pump, or said thermal transfer system and
at least one removable memory physically connected to said second section and adapted to record data respecting the actual operation of one or more of said one or more second section controllers or said air compressor.

14. The compression and thermal application device as set forth in claim 1 wherein said first electrical contact and said second electrical contact each include a plurality of individual contacts and wherein one individual contact of the plurality of individual contacts of either the first electrical contact or the second electrical contact is a unique contact which protrudes beyond any other individual contact contained in the same electrical contact as the unique contact and wherein as said first electrical contact and said second electrical contact are disconnected, a final connection between said first electrical contact and said second electrical contact occurs between said unique contact and at least one other individual contact.

15. The compression and thermal application device as set forth in claim 1 wherein said first electrical contact and said second electrical contact each include a plurality of individual contacts and wherein one individual contact of the plurality of individual contacts of either the first electrical contact or the second electrical contact is a unique contact which protrudes beyond any other individual contact contained in the same electrical contact as the unique contact and wherein at least one individual contact included on the electrical contact that does not include said unique contact is a resiliently biased individual contact that is resiliently biased in a direction toward said unique contact when said second section is docked with said first section such that as said first electrical contact and said second electrical contact are disconnected, a final connection between said first electrical contact and said second electrical contact occurs between said unique contact and said at least one resiliently biased individual contact.

16. The compression and thermal application device as set forth in claim 8 wherein one of said dock and said second section further includes at least one rail and the other of said dock and said second section further includes at least one guide that accommodates said rail such that said rail slides within said guide and said guide facilitates the proper alignment of said second section within said dock.

17. A compression and thermal application device as in claim 8 wherein said wheel is rotated past a neutral point, said resilient material in causes said piston to place a force on said wheel that in turn rotates said wheel without the need for any other application of force on said wheel.

18. A compression and thermal application device comprising:
a first section including a reservoir, a liquid pump, a thermal exchange system, a first section air compressor, at least one port in fluid communication with said reservoir, at least one port in fluid communication with said first section air compressor, one or more first section controllers and a first control panel in electrical communication with said on or more first section controllers;
a second section, physically separate from said first section, including an air compressor, at least one port in fluid communication with said air compressor, one or more second section controllers, and a second control panel in electrical communication with at least one of said second section controllers;
said first section further including:
a dock, said dock defining a cavity having an opening that accommodates said second section and wherein said at least one port of said second section is located on said second section such that when said second section is docked, said at least one port is exposed and accessible through said cavity;
a pawl;
a wheel having a lock surface, an exterior eccentrically mounted pin, and interior eccentrically mounted pin that extends into said dock; and
a lever arm having a case connected to said first section, a resilient material contained within said case and a piston having a first end that slides within said case and is biased by said resilient material in an outward direction, said piston further including a distal end connected to said wheel;
wherein insertion of said second section into said dock causes said interior eccentrically mounted pin to contact a portion of said second section causing said interior eccentrically mounted pin to rotate said wheel and wherein the rotation of said wheel as a result of the insertion of said second section into said dock causes said piston to apply a force to said resilient material and build potential energy in said resilient material such that when said lever arm passes a neutral position, potential energy in said resilient material is released resulting in further rotation of said wheel and further movement of said interior eccentrically mounted pin such that said pin transfers a force to said second section thereby further inserting said second section into said dock and bring said lock surface into contact with said pawl.

* * * * *

UNITED STATES PATENT AND TRADEMARK OFFICE
CERTIFICATE OF CORRECTION

| | | |
|---|---|---|
| PATENT NO. | : 8,979,915 B2 | Page 1 of 1 |
| APPLICATION NO. | : 13/089161 | |
| DATED | : March 17, 2015 | |
| INVENTOR(S) | : Michael L. Wilford et al. | |

It is certified that error appears in the above-identified patent and that said Letters Patent is hereby corrected as shown below:

In the Specification:

Column 2, line 16, delete "two charges" and insert --two chargers--;

Column 4, line 29, delete "control" and insert --control.--;

Column 6, line 37, delete "connections" and insert --connection--;

Column 7, line 42, delete "lest" and insert --least--;

In the Claims:

Claim 8, Column 14, line 38, delete "said on or more" and insert --said one or more--;

Claim 11, Column 15, line 44, delete "port is protrudes" and insert --port protrudes--;

Claim 12, Column 15, line 47, delete "port is protrudes" and insert --port protrudes--;

Claim 18, Column 16, line 41, delete "said on or more" and insert --said one or more--.

Signed and Sealed this
Eighth Day of September, 2015

Michelle K. Lee
*Director of the United States Patent and Trademark Office*